United States Patent [19]

Schön et al.

[11] Patent Number: 5,463,102
[45] Date of Patent: Oct. 31, 1995

[54] PROCESS FOR THE CONTINUOUS PRODUCTION OF ARYL CARBONATES

[75] Inventors: Norbert Schön; Johann Rechner, both of Krefeld; Paul Wagner, Düsseldorf; Hans-Josef Buysch, Krefeld; Hans-Erich Gasche, Odenthal; Ricarda Leiberich, Langen, all of Germany

[73] Assignee: Bayer Aktiengesellschaft, Leverkusen, Germany

[21] Appl. No.: 182,867

[22] Filed: Jan. 18, 1994

[30] Foreign Application Priority Data

Jan. 25, 1993 [DE] Germany ............................ 43 01 899.8

[51] Int. Cl.[6] .................................................... C07C 69/96
[52] U.S. Cl. ............................ 558/274; 558/271; 558/270
[58] Field of Search .................................... 558/274, 271, 558/270

[56] References Cited

U.S. PATENT DOCUMENTS

| | | | |
|---|---|---|---|
| 3,642,858 | 2/1972 | Frevel et al. | 558/274 |
| 4,045,464 | 8/1977 | Romano et al. | 558/270 |
| 4,079,038 | 3/1978 | Choi et al. | 558/270 |
| 4,182,726 | 1/1980 | Illuminati et al. | 558/270 |
| 4,330,665 | 5/1982 | Krimm et al. | 558/271 |
| 4,403,056 | 9/1983 | Gioleto et al. | 558/274 |
| 4,410,464 | 10/1983 | Hallgren | 558/271 |
| 4,552,704 | 11/1985 | Mark | 558/271 |
| 4,612,386 | 9/1986 | Renga | 558/274 |
| 4,973,728 | 11/1990 | Tuinstra et al. | 558/270 |
| 5,210,268 | 5/1993 | Fukuoka et al. | 558/270 |
| 5,218,078 | 6/1993 | Marks et al. | 558/270 |
| 5,233,072 | 8/1993 | Kricsfalussy et al. | 558/277 |
| 5,276,134 | 1/1994 | Tuinstra et al. | 528/371 |
| 5,284,965 | 2/1994 | Buysch et al. | 558/270 |
| 5,334,742 | 8/1994 | Schon et al. | 558/274 |

FOREIGN PATENT DOCUMENTS 0461274 12/1991 European Pat. Off. .
WO9218458 10/1992 WIPO .

OTHER PUBLICATIONS

Perry's Chemical Engineer's Hanbook, Sixth Edition, McGraw–Hill 1984, pp. 4–24–4–28.

Primary Examiner—Glennon H. Hollrah
Assistant Examiner—Deborah Lambkin
Attorney, Agent, or Firm—William C. Gerstenzang; Sprung Horn Kramer & Woods

[57] ABSTRACT

Organic carbonates containing at least one aromatic ester group can be obtained in a continuous manner from carbonates containing at least one aliphatic ester group and a phenolic compound in the presence of a transesterification catalyst known per se by carrying out the reaction in at least two stirred containers connected one behind the other in such a way that, in each case, the phenolic compound is metered in liquid form into the first stirred container and the carbonate containing at least one aliphatic ester group is metered in liquid form into one or more of the stirred containers. The carbonate containing at least one aromatic ester group is removed in liquid form from the last stirred container. Volatile reaction products, for example alcohol which has been cleaved out or a dialkyl carbonate are removed in gaseous form from one or more stirred containers.

20 Claims, 2 Drawing Sheets

PROCESS FOR THE CONTINUOUS PRODUCTION OF ARYL CARBONATES

BACKGROUND OF THE INVENTION

1. Field of the Invention

The invention relates to a process for the continuous production of aryl carbonates from carbonates containing at least one aliphatic ester group and phenols, on the one hand, and from alkyl aryl carbonates, on the other hand, by catalysed transesterification, in which process the reaction is carried out in at least two stirred containers connected one behind the other.

The production of aromatic and aliphatic-aromatic carbonic acid esters (carbonates) by transesterification starting from aliphatic carbonic acid esters and phenols is known in principle. It is an equilibrium reaction in which the position of the equilibrium is displaced almost completely in the direction of the aliphatically substituted carbonates. It is therefore comparatively easy to produce aliphatic carbonates from aromatic carbonates and alcohols. In order to carry out the reaction in the reverse sense in the direction of aromatic carbonates, it is necessary to displace the very unfavourably situated equilibrium efficiently, not only a very active catalyst compound but also a favourable procedure having to be used.

2. Description of the Related Art

A multiplicity of efficient catalysts, such as, for example, alkali metal hydroxides, Lewis acid catalysts from the group comprising the metal halides (German Offenlegungsschrift 2 528 412 and 2 552 907), organotin compounds (European Patent Specification 0 000 879, European Patent Specification 0 000 880, German Offenlegunsschrift 3 445 552, European Patent Specification 0 338 760), lead compounds (Japanese Patent Specification 57/176 932) and Lewis acid/ protonic acid catalysts (German Offenlegungsschrift 3 445 553) are recommended for the transesterification of aliphatic carbonic acid esters with phenols.

In the known processes, the transesterification is carried out in a reactor which is operated batchwise at atmospheric pressure or under pressure, if necessary with an additional separating column. In these processes, reaction times of many hours are needed before even only moderate conversions of approximately 50% phenol are achieved even with the most active catalysts. Thus, in the transesterification of phenol with diethyl carbonate at 180° C. with batchwise operation using various organotin compounds such as those described in German Offenlegungsschrift 3 445 552, yields of diphenyl carbonate in an order of magnitude of more than 20% are achieved only after an approximately 24-hour reaction time; in the transesterification of phenol and dimethyl carbonate with batchwise operation with the aid of organotin catalysts such as those described in European Patent Specification 0 000 879, the phenol conversion is 34% of the theoretical value after 30 h.

This means that, owing to the unfavourable thermodynamic conditions, the transesterification reactions described with batchwise operation can be carried out only very disadvantageously for the purpose of an industrial process even if very active catalyst systems are used since very poor space-time yields and high dwell times at high reaction temperatures are necessary.

Such procedures are also particularly disadvantageous since, even with very selective transesterification catalysts, an appreciable proportion of side reactions, for example the formation of ethers and the cleaving of carbon dioxide, occur at the high temperatures and with long dwell times of many hours.

An attempt has therefore been made to displace the reaction equilibrium as quickly as possible in the direction of the products by adsorption of the alcohol produced during the transesterification on molecular sieves (German Offenlegungsschrift 3 308 921). The description of this procedure reveals that the adsorption of the reaction alcohol requires a large amount of molecular sieve which exceeds by far the amount of the alcohols liberated. Furthermore, the molecular sieves used have to be regenerated even after a short time and the rate of conversion to the alkyl aryl carbonate intermediates is relatively low. This process, too, therefore appears not to be advantageously applicable industrially and economically.

A continuous transesterification process for the production of aromatic carbonates in which the reaction is carried out in one or more multistage distillation columns is claimed in EP-A 0 461 274. In this case, phenols are first reacted with dialkyl carbonates to form aryl carbonate mixtures which essentially contain alkyl aryl carbonates. These are then further reacted to form the desired diaryl carbonate end products in a second, downstream column. The applicant stresses the efficiency and the selectivity of his procedure. This is contradicted by the relatively low space-time yields, specified in the examples, of the reaction of phenols with diaryl carbonates, these having been achieved under optimum conditions at high temperatures and pressures with the best transesterification catalysts. In the specified procedure which emerges from the examples, the further reaction of the alkyl acryl carbonates to form diaryl carbonates proceeds as a disproportionation reaction. It is therefore not surprising that substantially better space-time yields are achieved in this reaction which proceeds rapidly compared with the first transesterification stage.

The object of an improvement of the transesterification reaction should therefore be a further acceleration, especially of the transesterification stages with phenol, but the selectivity of the entire process should not be reduced.

Surprisingly, it has now been found that this is achieved in a continuously run transesterification process in stirred-kettle cascades, although the particular efficiency and the mild conditions of the column procedure in contrast to the kettle procedure are stressed and given prominence in EP-A 0 461 274.

Markedly higher space-time yields of the alkyl aryl carbonate formation than disclosed in EP-A 0 461 274 can be achieved with the continuous procedure according to the invention in stirred kettles connected one behind the other even at normal pressure and substantially lower temperatures. In view of the arguments put forward in EP-A 0 461 274 (page 5, line 39 ff.), however, the fact that these higher conversion rates are achieved with very high selectivity of the reactions of >99% is quite particularly surprising. The procedure according to the invention therefore must also be assessed as particularly advantageous because very simple and easily controllable technology using standard equipment is used. The design of such equipment and the extrapolation of a continuously operated stirred-kettle process to the industrial scale is relatively easy for the person skilled in the art to carry out. Temperature, pressure and dwell time spectrum of the reactants can easily be adjusted over a wide range, with the result that a variable procedure is also available. The heat input necessary for the endothermically proceeding transesterification reaction can be achieved here without problems.

SUMMARY OF THE INVENTION

The invention accordingly relates to a process for the production of an aromatic carbonate of the formula $$R^1-O-CO-O-R^2 \quad (I)$$

in which

R² is phenyl or naphthyl and a mono- to trisubstituted straight-chain or branched $C_1-C_4$-alkyl-, straight-chain or branched $C_1-C_4$-alkoxy-, cyano- and/or halogen-substituted phenyl or naphthyl, and R¹ independently of R², assumes the scope of meaning of R² or a straight-chain or branched $C_1-C_6$-alkyl, by catalysed reaction of 0.1 to 10 mol, preferably 0.2 to 5 mol, particularly preferably 0.5 to 3 mol of an organic carbonate containing at least one aliphatic ester group of the formula $$R^1-O-CO-O-R^3 \quad (II)$$

in which

R³ is straight-chain or branched $C_1-C_6$-alkyl and

R¹ has the above scope of meaning, with 1 mol of a phenolic compound of the formula $$R^2-OX \quad (III)$$

in which

R² has the above scope of meaning and

X represents hydrogen or $-CO-O-C_1-C_6$-alkyl containing a straight-chain or branched alkyl group, in the presence of a transesterification catalyst known at 80° to 350° C., characterized in that the reaction is carried out in at least two stirred containers connected one behind the other in such a way that the phenolic compound of the formula (III) is metered in liquid form into the first stirred container and the organic carbonate of the formula (II) is metered into one or more stirred containers, preferably, however, only into the last stirred container, and the reaction product of the formula (I) is removed in liquid form from the last stirred container, if necessary after traversing a dwell-time section, and the products of the formula $$R^3-OX \quad (IV)$$

in which R³ and X have the specified meaning, are removed at the head of one or more stirred containers, preferably at the head of the first stirred container.

DETAILED DESCRIPTION OF THE INVENTION

Figure 1:
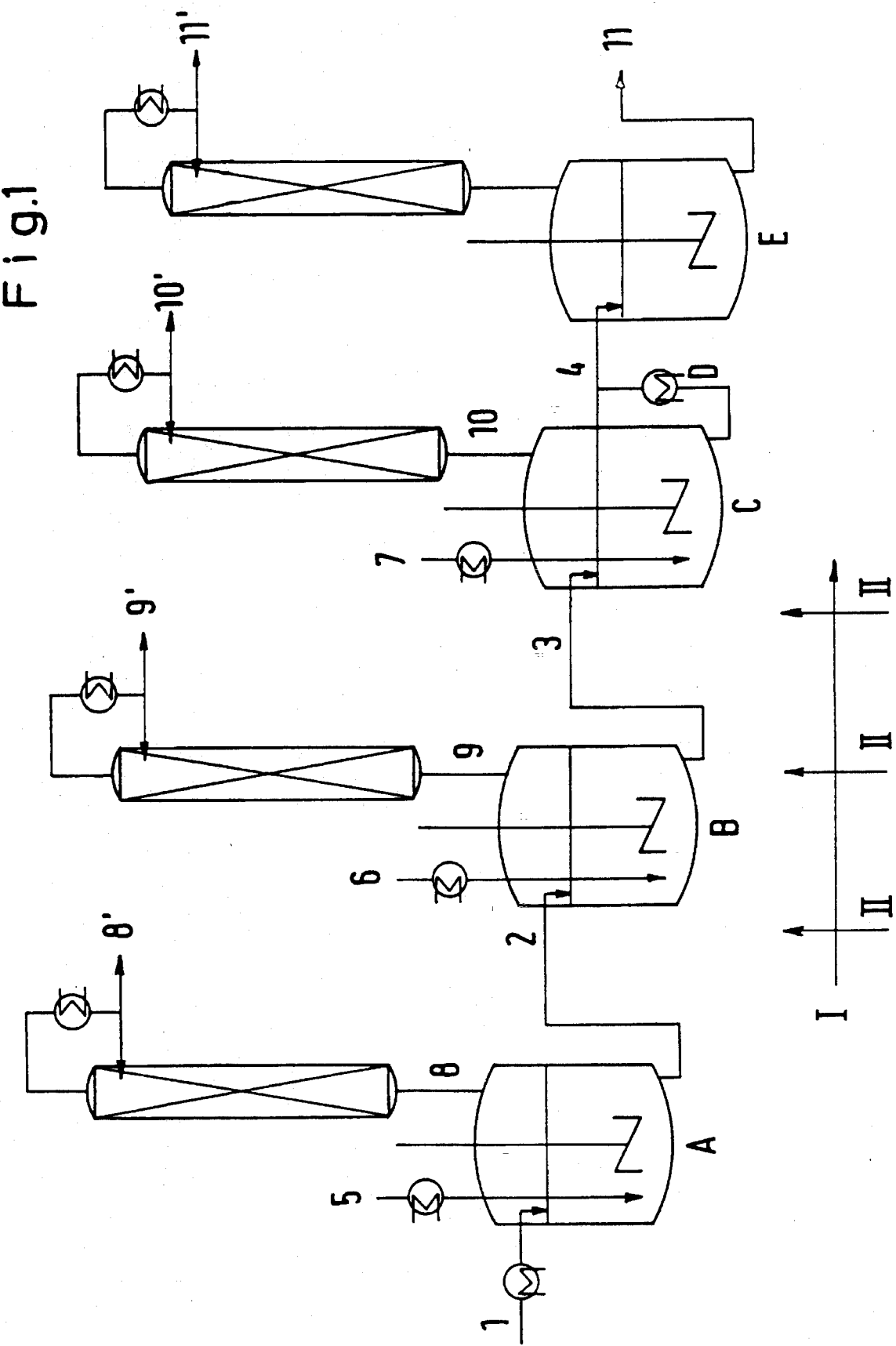
FIGS. 1 and 2 show cascades of stirred containers to therein carry out the claimed process. The starting products are either in cross (transverse) current (FIG. 1) or in counter-current (FIG. 2).

The transesterification by the process according to the invention comprises a plurality of reactions, as the following equations show in generalized form (Alk=alkyl; Ar=aryl):

$$\text{Alk}-O-CO-O-\text{Alk}+\text{Ar}-OH \rightarrow \text{Alk}-O-CO-O-\text{Ar}+ \text{Alk}-OH \quad \text{(Equation 1)}$$

$$\text{Alk}-O-CO-O-\text{Ar}+\text{Ar}-OH \rightarrow \text{Ar}-O-CO-O-\text{Ar}+ \text{Alk}-OH \quad \text{(Equation 2)}$$

$$2 \text{ Ar}-OCOO-\text{Alk} \rightarrow \text{Ar}-OCOO-\text{Ar}+ \text{Alk}-OCOO-\text{Alk} \quad \text{(Equation 3)}$$

In the case of the formation of a diaryl carbonate, the transesterification of the aliphatic to the aromatic ester groups takes place in two stages, an alkyl aryl carbonate being traversed as product of the first transesterification stage along the lines of equation 1.

Equation 3 furthermore shows a disproportionation reaction in which both the symmetrical dialkyl carbonate and the desired symmetrical diaryl carbonate are produced from a mixed alkyl aryl carbonate. It is furthermore possible to obtain the alkyl aryl carbonate as the desired reaction product, that is to say only to operate the first transesterification stage. It is in addition furthermore possible also to obtain asymmetrical diaryl carbonates by using mixtures of different phenols.

Dialkyl carbonates having identical or different aliphatic ester groups containing straight-chain or branched $C_1-C_6$-alkyl are used. Such dialkyl carbonates are known to the person skilled in the art and can be produced by known processes. For cost reduction reasons, the starting point will generally be symmetrical dialkyl carbonates.

Straight-chain or branched $C_1-C_6$-alkyl is, for example, methyl, ethyl, propyl, isopropyl, butyl, isobutyl, pentyl or hexyl, preferably methyl or ethyl, particularly preferably methyl.

Straight-chain or branched $C_1-C_4$-alkoxy is, for example, methoxy, ethoxy, propoxy, isopropoxy, butoxy or isobutoxy, preferably methoxy.

Halogen is, for example, fluorine, chlorine or bromine, preferably fluorine or chlorine, particularly preferably chlorine.

The aromatic ester group may be derived from a phenol or a naphthol, preferably from a phenol, and may, in the specified manner, be mono- to trisubstituted, preferably mono- or disubstituted, particularly preferably monosubstituted. The cyano substituent as a rule occurs only singly as substituent. The process according to the invention is of quite particular significance for the transesterification of unsubstituted phenol.

Phenols which can be used according to the invention and which come within the scope of the formula (III) if X represents hydrogen are, for example, unsubstituted phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol and 2-naphthol.

Accordingly, phenolic compounds which can preferably be used are generally those of the formula $$R^{12}-OH \quad (V),$$

in which

R¹² is phenyl, or phenyl monosubstituted by $C_1-C_4$-alkyl, $C_1-C_4$-alkoxy or chlorine.

Of these, the unsubstituted phenol is particularly preferred.

Preferably, symmetrical dialkyl carbonates of the formula $$R^3-O-CO-O-R^3 \quad (VI),$$

in which

R³ has the specified meaning, are used as organic carbonates containing at least one aliphatic ester group.

Dialkyl carbonates which can be used according to the invention are, for example, dimethyl carbonate, diethyl carbonate, dipropyl carbonate, dibutyl carbonate and dihexyl carbonate. Dialkyl carbonates which can preferably be used are dimethyl carbonate and diethyl carbonate, particularly preferably dimethyl carbonate.

The organic carbonate (II) containing at least one aliphatic ester group can be used as such in the process according to the invention. It is, however, possible and represents a preferred variant, to use this organic carbonate in a mixture containing small amounts of the basic alcohol $R^3$—OH. The alcohol $R^3$OH occurs as a cleavage product in the process according to the invention and represents the special case of the formula (IV) in which X=H. Accordingly, the cleavage products comprising carbonate (X=—CO—O—$C_2$-$C_6$-alkyl) and alcohol (X=H) do not have to be completely separated for the purpose of returning the carbonate to the process according to the invention; this represents an energy advantage. The amount of alcohol permitted in the mixture containing the carbonate is 0–5% by weight, preferably 0.1–3% by weight, particularly preferably 0.15–2% by weight, based on the amount of the carbonate used. The zero lower limit denotes the procedure employing pure carbonate.

Diaryl carbonates which can be produced according to the invention are, for example, diphenyl carbonate, the symmetrically and asymmetrically substituted isomeric bis(methylphenyl) carbonates, the symmetrically and asymmetrically substituted isomeric bis(chlorophenyl) carbonates, the symmetrically and asymmetrically substituted isomeric bis(methoxyphenyl) carbonates, the symmetrically and asymmetrically substituted isomeric bis(ethoxyphenyl) carbonates, bis(2,6-dimethylphenyl) carbonate, bis(2,4-dimethylphenyl) carbonate, di-1-naphthyl carbonate and di-2-naphthyl carbonate, and also further asymmetrically substituted diaryl carbonates, for example the isomeric (methylphenyl)phenyl carbonates, the isomeric (chlorophenyl)phenyl carbonates, the isomeric (methoxyphenyl)phenyl carbonates, the isomeric naphthyl phenyl carbonates and 1-naphthyl-2-naphthyl carbonate.

Preferred diaryl carbonates which can be prepared according to the invention are those of the formulae

or

in which $R^{12}$ and $R^{15}$ have, independently of one another, the scope of meaning specified above for $R^{12}$ A diaryl carbonate which can be particularly preferably produced is diphenyl carbonate.

Alkyl aryl carbonates which can be produced according to the invention are, for example, $C_1$-$C_6$-alkyl phenyl carbonates, such as methyl phenyl carbonate, ethyl phenyl carbonate, propyl phenyl carbonate, butyl phenyl carbonate and hexyl phenyl carbonate, $C_1$-$C_6$-alkyl (o-, m-, p-methylphenyl) carbonate, such as methyl o-methylphenyl carbonate, methyl p-methylphenyl carbonate, ethyl o-methylphenyl carbonate, ethyl p-methylphenyl carbonate, $C_1$-$C_6$-alkyl (o-, m-, p-chlorophenyl) carbonates, such as methyl or ethyl (p-chlorophenyl) carbonate and analogous compounds. Alkyl aryl carbonates which can be particularly preferably produced are methyl phenyl carbonate and ethyl phenyl carbonate, quite particularly preferably methyl phenyl carbonate.

To blend the reaction components, the stirred containers to be used according to the invention are equipped with stirring tools which can be used for this purpose. Such stirrers are known to the person skilled in the art. Mention may be made by way of example of: disc agitators, impeller mixers, propeller mixers, paddle stirrers, multistage impulse countercurrent agitators and interference multistage pulse countercurrent agitators, pipe ejector mixers and other ejector mixer types. Preferred stirrers are those which make possible an efficient blending of gases and liquids, for example ejector mixers, such as pipe ejector mixers and triangular mixers, propeller mixers, turbine agitators etc.

For better blending, the stirred containers can preferably be provided with flow-breaker internals. Said flow breakers may be designed at the same time for introducing or for removing heat from the reactor in a temperature-controllable manner.

The heat necessary for the reaction may be introduced with the starting products. It is, however, preferable to introduce additional energy into the reactor, for example via a jacket heating system or through internal heating elements.

The stirred containers concerned may be equipped with temperature measurement points, sampling points and other measurement and control elements.

According to the invention, at least two, for example 2 to 10, stirred containers connected one behind the other are used. It is, however, preferable to use 3 to 10, and particularly preferable to use 3 to 8 stirred containers connected one behind the other.

Figure 2:
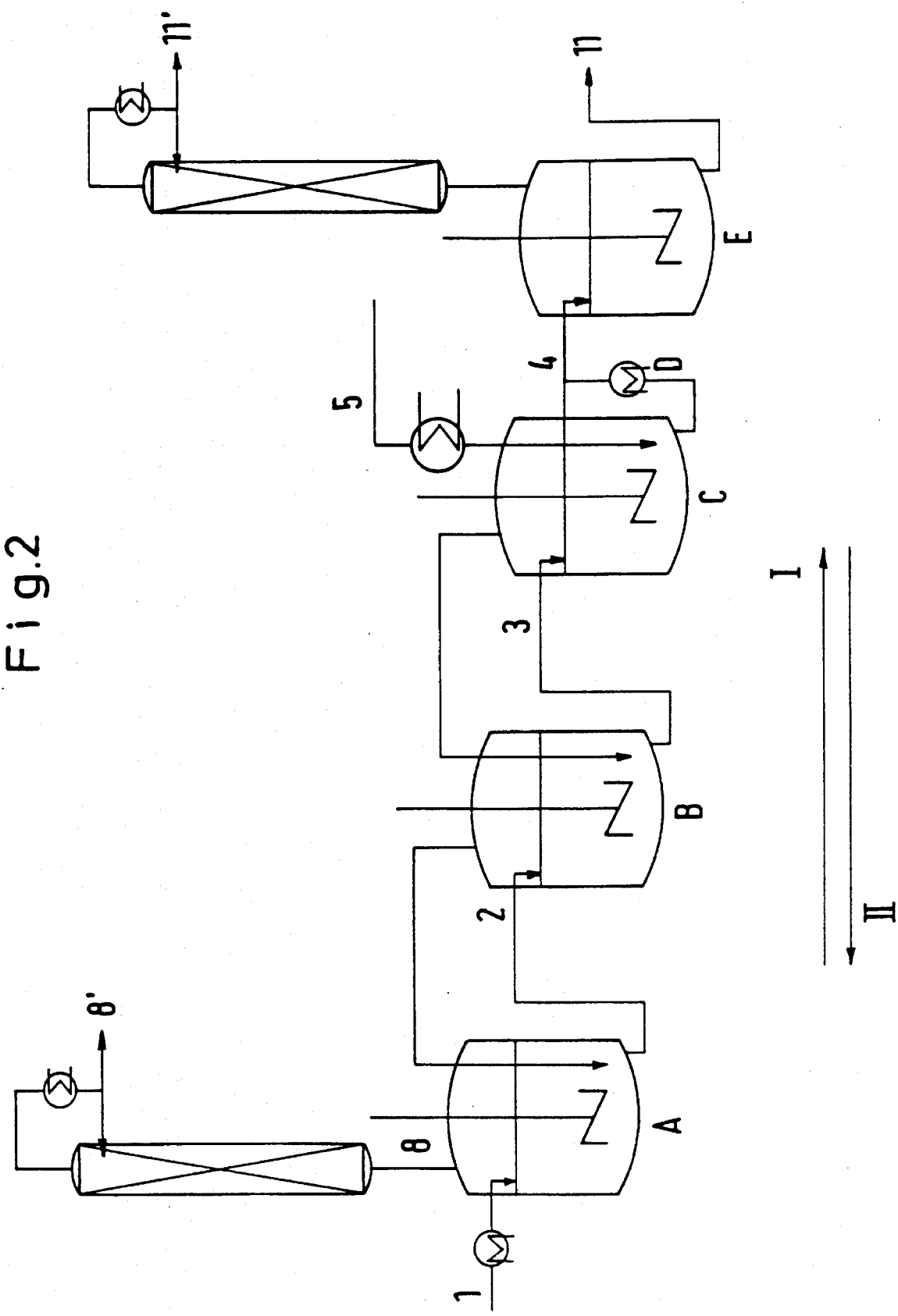

FIGS. 1 and 2 show by way of example various embodiments of the invention. Numbers and letters specified in the text relate to these diagrams.

The reaction component of the formula (III) to be metered in at the first stirred container A may, if necessary, be preheated to the reaction temperature envisaged in an upstream heater element. It can be introduced in liquid form at any point, for example via pipe (1) in FIG. 1 or 2, or through a tube (5) in FIG. 1, into the liquid phase below the stirrer.

The liquid phase to be removed from the stirred container concerned can be removed at a suitable point in the container, for example in the upper third or via a syphon (2) and (3) in FIGS. 1 and 2 which can, if necessary, be heated and can be adjusted in height and fed into the stirred container B or C which is downstream in each case. At the same time, a predetermined filling level should be achieved in the container concerned. The technologies to be used for the continuous operation of kettle cascades are prior art and are known to the person skilled in the art.

The organic carbonate of the formula (II) is passed in gaseous form through the continuously running liquid flow I either in cross(transverse) current (FIG. 1) or, preferably, in countercurrent (FIG. 2).

In this case, cross(transverse) current means that the starting products of the formula (II) are in each case metered in at each stirred container A, B, and C ((5), (6), (7) in FIG. 1) and are in each case removed again at the head of each stirred container ((8), (9), (10) in FIG. 1), i.e. the starting products of the formula (II) flow through the stirred containers transversely to the direction of flow of the liquid phase. At the same time, the total amount of the starting products of the formula (II) to be metered in can be distributed in any desired manner over the individual stirred containers.

The countercurrent procedure (FIG. 2), which is preferably to be used, means that the starting products of the formula (II) are metered in at the last stirred container (C in FIG. 2) via pipe (5), continuously fed counter to the liquid phase flowing from the first to the last stirred container and removed at the head of the first stirred container (A in FIG. 2) via pipe (8).

The starting products of the formula (II) may in both cases either be metered in in liquid form and evaporated by the liquid phase present or, preferably, evaporated in an upstream apparatus and introduced into the stirred container concerned in gaseous form. In this connection, the metering-in may take place either into the liquid phase or into the gas space above it. The mixing of the gas phase and liquid phase is achieved by suitable mixing devices, which are mentioned above and known to the person skilled in the art. If gas-introducing stirrers having a hollow shaft are used, the gas phase may also be directly metered into the hollow shaft of the gas-introducing stirrer.

The reaction products of the formula (IV) to be removed at the head of the stirred container concerned can be taken off, for example, in gaseous form via (8'), (9'), (10') and (11').

In this connection, it is possibly advantageous to separate off higher-boiling reaction constituents, for example products of the formula (I) or starting products of the formula (III), by suitable dephlegmation or by a column mounted on top and feed them back into the stirred container concerned. The products of the formula (IV) can thus be introduced into a suitable separating appliance, for example without condensation. In the case of the reaction of dimethyl carbonate with phenol, this may be a pressure distillation column for separating the dimethyl carbonate/methanol mixture produced, as is known to the person skilled in the art. The dimethyl carbonate produced in this process, which possibly still contains small amounts of methanol, can be fed back into the transesterification process as starting product of the formula (II).

It is also possible to take off and to condense the products of the formula (IV), possibly after separating off higher-boiling reaction constituents, as described above. A purification and separation of the product stream can then be carried out in a suitable manner known to the person skilled in the art.

In a downstream stripping section D, the product stream to be removed in liquid form at the last reactor C may, if necessary, be separated from low-boiling constituents, for example the starting products of the formula (II) or the products of the formula (IV), the latter being fed back to the last stirred container C. The product stream removed in liquid form can be worked up and purified by standard methods, for example by distillation.

In a further procedure, the product stream to be removed in liquid form may be fed into 1 to 5, preferably 1 to 3, dwell-time containers E which are, if necessary, stirred or fed with inert gas, in which case further reactions as in equation 2 and/or equation 3 may proceed therein. In this case, the aromatic carbonate of the formula (I) is removed at (11) and volatile reaction products produced in E are removed at (11').

The last dwell-time container E in each case may, if necessary, have a downstream stripping section with which low-boiling products of the formula (IV) and/or unreacted starting products of the formula (III) can be fed back in their entirety or partly into said dwell-time container E. It may also be advantageous to separate off the volatile reaction products of the formula (IV) to be removed at the head of the first dwell-time container E, for example via (11') by means of a rectifier or dephlegmator section mounted at that point from higher-boiling products of the formula (I) or starting products of the formula (III) and feed them back into E.

In a further variant, the dwell-time container E is constructed in the form of a distillation apparatus which is operated as a "reaction distillation", that is to say a distillation of the substances involved is carried out simultaneously with the reaction which is proceeding.

The features which are essential for a "reaction distillation" for the purpose of the invention are the following: the alkyl aryl carbonate intermediate which is still unreacted is substantially prevented from leaving the reaction sector of the reaction in the upward or downward direction by a specially chosen temperature gradient in the distillation apparatus. The readily volatile reaction products of the formula (IV) are removed at the head of the column, while the low-volatility reaction product, in this case the diaryl carbonate, is removed at the base of the column. Any excess phenol which may be present may be removed either together with the diaryl carbonate end products at the base of the distillation apparatus or together with the low-boiling products at the head of the apparatus.

The reactor described as "reaction column" comprises a column-type tube to which a temperature profile is applied which, viewed from top to bottom, comprises an increasing temperature range from 60° to 320° C., preferably 65° to 305° C., and particularly preferably from 65° to 250° C. To adjust the temperature gradients in the individual sections of the column-type reactor, said sections may be provided with an insulation or with a thermostatic system. In this connection, the thermostatic system may be a heating system or a cooling system as required. The reaction column may be widened or narrowed in various sections of its entire length in accordance with the gas and liquid loads and the required dwell times.

For the central section of the reaction column, the reaction region, fixed internals are preferred, but for those parts in which separations take place, filler materials and fixed packings are preferred.

One or more evaporators, separated if necessary by adiabatically insulated column sections, are arranged at the lower end of the reaction column. Said evaporators may be arranged inside or, preferably, outside the column. In an industrial design, apparatuses which are standard in the technology, such as circulation evaporators, falling-film evaporators and coil evaporators are used.

Above the evaporator zone, in the central region described as "reaction zone", preferably fixed internals and, particularly preferably, those having high liquid hold-up, for example bubble-cap trays with high overflow weirs as described in German Patent Specification 2 503 195, are used. The theoretical number of trays in this region is 1 to 50, preferably 2 to 25, and particularly preferably, 2 to 15.

Again above this region, the column is equipped with further filling bodies or internals which are particularly suitable for distillative substance separations. A rectifier section with which a controlled reflux of the column can be established is preferably situated at the upper end of the column.

The reaction column is operated in such a way that product stream removed in liquid form from the stirred container cascade is metered in in liquid form above the reaction zone. This stream passes through the reaction zone and is partly converted into diaryl carbonate therein and the still unreacted reactants are conveyed back in gaseous form into the reaction zone and the upper sections of the column with the aid of the evaporators described. They condense therein and are again reacted to form diaryl carbonate end product. The diaryl carbonate end product is enriched as highest-boiling reaction component in the bottom region of the column and fed out at that point together with catalyst, which may be homogeneously dissolved, and small amounts of alkyl phenyl carbonate and aromatic hydroxyl compound.

The low-boiling reaction products of the formula (IV) are removed at the head of the column. The phenols of the formula (III) which are present in excess or are unreacted can be fed out either at the base of the column together with the diaryl carbonate end product of the formula (I) or, in a preferred procedure, together with the low-boiling products at the head of the column.

The product stream, which is removed in liquid form at the last reactor C or dwell-time container E and which contains the products of the formula (I), can be fed, in a further particular version of the invention, back into the first reactor container A instead of the starting product of the formula (III) after interim storage in suitable containers. This may also be possible several times, in which case the feed of the second starting product of the formula (II) may possibly also be omitted. To carry out such a procedure continuously, either at least two storage containers or a storage container having at least two chambers is necessary, the product from the reaction in progress being fed into the first chamber and the starting product for the reaction in progress being removed from the second chamber. Once a chamber has been emptied or a chamber has been filled, the second chamber is used to receive the product from the kettle cascade and the first chamber is used to feed the starting product into the kettle cascade.

In a further procedure, in addition to the starting products, a solvent or gas which is inert under the reaction conditions can be fed in at any desired point in the apparatus. Such inert solvents are, for example, hydrocarbons, such as hexane, heptane, isooctane, cyclohexane, methylcyclohexane, toluene, xylenes, chlorobenzenes, tetralin, decalin etc. Suitable inert gases are, for example, carbon dioxide, nitrogen, noble gases etc.

The transesterification catalysts to be used and known per se are preferably introduced into the stirred container in dissolved or suspended form together with the starting products of the formula (II) to be metered in in liquid form. Alternatively, the catalyst may also be metered in separately or in dissolved or suspended form in a small amount of the starting product of the formula (III) or in a suitable inert solvent which is extraneous to the system (see above). If heterogeneous catalysts are used, these can also be used directly in a stationary manner in the stirred container.

The discharge of the catalysts must be prevented by suitable filtering appliances.

It is important that a catalyst is present at least in 2 stirred containers.

If non-stationary catalysts are used, it is possible to feed back the catalysts into the reaction process again after partial or complete separation of the products or starting products as described above, and, if necessary, a portion of the catalyst corresponding to the amount of deactivated catalyst is separated off and is replaced by fresh catalyst.

The process according to the invention is carried out at temperatures in the liquid phase from 80° to 350° C., preferably at 100° to 250° C. and, particularly preferably, at temperatures from 120° to 240° C. At the same time, the liquid phase temperature in the stirred containers should not be above the evaporation point of the phenolic compound of the formula (III) used. It may therefore be advantageous to carry out the transesterification according to the invention in the region of the stirred containers not only at normal pressure but also at increased or reduced pressure in the range from 10 mbar to 20 bar. A preferred temperature range is between 0.05 and 15 bar, a particularly preferred pressure range being between 0.08 and 10 bar.

Catalysts which are suitable for the process according to the invention and which may be identical for all the phases of the process according to the invention are known in the literature. Such catalysts are, for example, hydrides, oxides, hydroxides, alcoholates, amides or salts of alkali (alkaline-earth) metals, such as lithium, sodium, potassium, rubidium, caesium, magnesium and calcium, preferably of lithium, sodium, potassium, magnesium and calcium, particularly preferably of lithium, sodium and potassium (U.S. Pat. Nos. 3,642,858, 3,803,201, European Patent Specification 1082). If the alcoholates are used, these may also be formed according to the invention in situ by using the elemental alkali metals and the alcohol according to the invention which is to be reacted. Salts of the alkali(alkaline-earth) metals may be those of organic or inorganic acids, such as those of acetic acid, propionic acid, butyric acid, benzoic acid, stearic acid, carbonic acid (carbonates or hydrogencarbonates), hydrochloric acid, hydrobromic or hydroiodic acid, nitric acid, sulphuric acid, hydrofluoric acid, phosphoric acid, hydrocyanic acid, thiocyanic acid, boric acid, stannic acid, $C_1$–$C_4$-stannoic acids or antimonic acids. Preferably, the oxides, hydroxides, alcoholates, acetates, propionates, benzoates, carbonates and hydrogen carbonates are suitable as compounds of the alkali (alkaline-earth) metals, and hydroxides, alcoholates, acetates, benzoates or carbonates are particularly preferably used.

Such alkali(alkaline-earth) metal compounds (possibly formed in situ from the free alkali metals) are used in amounts of 0.001 to 2% by weight, preferably 0.005 to 0.9% by weight, particularly preferably 0.01 to 0.5% by weight, based on the reaction mixture to be reacted.

Further catalysts which can be used according to the invention are Lewis-acidic metal compounds such as $AlX_3$, $TiX_3$, $UX_4$, $TiX_4$, $VOX_3$, $VX_5$, $ZnX_2$, $FeX_3$ and $SnX_4$, where X represents halogen, acetoxy or aryloxy (German Offenlegungsschrift 2 528 412, 2 552 907), for example titanium tetrachloride, titanium tetraphenoxide, titanium tetraethoxide, titanium tetraisopropylate, titanium tetradodecylate, tin tetraisooctylate and aluminium triisopropylate, and furthermore organotin compounds of the general formula $(R^4)_{4-x}$—$Sn(Y)_x$, in which Y represents an $OCOR^5$, OH or $OR^5$ radical, where $R^5$ is $C_1$–$C_{12}$-alkyl, $C_6$–$C_{12}$-aryl or $C_7$–$C_{13}$-alkylaryl and $R^4$ can assume, independently of $R^5$, the scope of meaning of $R^5$ and x is an integer from 1 to 3, dialkyltin compounds containing 1 to 12 carbon atoms in the alkyl radical or bis(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctylate, octyltin triisooctylate, butylstannoic acid and octylstannoic acid in amounts of 0.001 to 20% by weight (European Patent Specification 879, European Patent Specification 880, European Patent Specification 39 452, German Offenlegunsschrift 3 445 555, Japanese Patent Specification 79/62 023), polymeric tin compounds of the formula —[$R^4$, $R^5$Sn—O—]—, for example poly[oxy(dibutylstannylene)], poly[oxy(dioctylstannytene)], poly[oxy(butylphenylstannylene)] and poly[oxy(diphenylstannylene)] (German Offen-legungsschrift 3 445 552), polymeric hydroxystannoxanes of the formula —[$R^4$Sn(OH)—O—]—, for example poly(ethylhydroxystannoxane), poly(butylhydroxy-stannoxane), poly(octylhydroxystannoxane), poly(undecylhydroxystannoxane) and poly(dodecyl-hydroxystannoxane) in amounts of 0.001 to 20% by weight, preferably of 0.005 to 5% by weight, based on carbonic acid diester (German Patent Specification 4 006 520). Further tin compounds which can be used according to the invention are tin(II) oxide or they have the formula

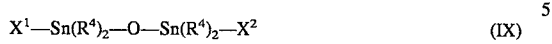

$$X^1\text{—}Sn(R^4)_2\text{—}O\text{—}Sn(R^4)_2\text{—}X^2 \qquad (IX)$$

wherein $X^1$ and $X^2$ are, independently of one another, OH, SCN, $OR^4$, $OCOR^4$ and halogen and $R^4$ is alkyl or aryl (European Patent Specification 338 760).

Suitable as further catalysts which can be used according to the invention are lead compounds, possibly together with triorganophosphanes, a chelate compound or an alkali metal halide, for example $Pb(OH)_2\cdot 2PbCO$, $Pb(OCO\text{—}CH_3)_2$, $Pb(OCO\text{—}CH_3)_2\cdot 2LiCl$, $Pb(OCO\text{—}CH_3)_2\cdot 2PPh_3$ in amounts of 0.001 to 1, preferably of 0.005 to 0.25 mol per mole of carbonate (Japanese Patent Specification 57/176 932, Japanese Patent Specification 01/093 580), other lead(II) and lead(IV) compounds, such as PbO, $PbO_2$, menium, plumbites ($PbO_2^{2-}$) and plumbates ($PbO_3^{2-}$) (Japanese Patent Specification 01/093 560), iron(III) acetate (Japanese Patent Specification 61/172 852), and furthermore copper salts and/or metal complexes, for example of alkali metals, zinc, titanium and iron (Japanese Patent Specification 89/005 588), combinations of Lewis acids and protonic acids (German Offenlegungsschrift 3 445 553) or elemental compounds of Sc, Cr, Mo, W, Mn, Au, Ga, In, Bi, Te and lanthanides (European Patent Specification 338 760).

Furthermore, heterogeneous catalyst systems can be used in the process according to the invention. These are, for example, mixed oxides of silicon and titanium, which can be produced by combined hydrolysis of silicon and titanium halides (Japanese Patent Specification 54/125 617), and titanium dioxides having high BET surface of >20 $m^2/g$ (German Offenlegungsschrift 4 036 594).

Catalysts which can preferably be used in the process according to the invention are tin, titanium and zirconium compounds and the abovementioned alkali and alkaline-earth compounds, and catalysts which can be used particularly preferably are organotin compounds and titanium tetraalcoholates and tetraphenolates.

The catalyst amounts to be used are 0.01 to 10 mol %, preferably 0.05 to 5 mol % and particularly preferably 0.01 to 2 mol %, based on the phenol or alkylaryl carbonate component used, and may to some extent differ from the amounts specified in the literature.

The following examples are intended to illustrate the present invention specifically, but the invention is not intended to be limited to these examples.

EXAMPLES

Example 1 (in accordance with FIG. 2 without stirred container E)

Three double-jacket vessels heated with oil and each having an internal volume of 1 l were connected one behind the other in such a manner that the liquid phase was injected at the base of the first reactor, removed from the first reactor via a siphon which was adjustable in height and fed in again at the base of the next reactor. The liquid phase was removed at the third reactor via a siphon. The gas phase was fed into the third reactor, removed again at the head and conveyed further into the upstream reactor. Gas phase and liquid phase were blended in the individual reactors by fast running gas-introducing mixers (1500 rev/min). The gas phase was removed at the head of the first reactor via a 30 cm long column filled with Raschig rings with a column head mounted on top, which column head made it possible to adjust a reflux onto the column. The metering and connecting pipes were temperature-controlled using heated strips in such a way that both the crystallization of the liquid phase and the condensation of the gas phase was prevented in these pipes.

The reactors were filled with 600 ml of phenol in each case and the reactor jackets were temperature-controlled at 180° C. with oil. 510 g/h of a mixture of 98.6% by weight of phenol and 1.4% by weight of octylstannoic acid (liquid phase) were metered continuously into the first reactor via a heated pump and, at the same time, 500 g/h of dimethyl carbonate, which was continuously evaporated in an electrically heated tube, were fed into the third reactor. After 5 h, the reaction was in stationary equilibrium, i.e. the composition of the liquid phases in the individual reactors and the product composition was no longer changing. 579 g/h of product mixture containing 60 g/h methyl phenyl carbonate and 12 g/h diphenyl carbonate were then removed continuously at the third reactor. The remainder to 100% was phenol, a small amount of dimethyl carbonate and catalyst.

453 g/h of product mixture composed of methanol and dimethyl carbonate were removed at the head of the column mounted on the first reactor. This gives a space-time yield for the methyl phenyl and diphenyl carbonate formation of 24 $g\times l^{-1}h^{-1}$. The selectivity in relation to the formation of aromatic carbonates was >99.9%.

Example 2

In the apparatus described in Example 1 (FIG. 2 without E) and under the reaction conditions specified there, 1.45 kg/h of a mixture of 97.8% by weight of phenol and 2.2% by weight of titanium tetraphenolate was continuously fed in at the base of the first reactor and 1.35 kg/h dimethyl carbonate was continuously fed in at the head of the third reactor. After approximately 5 h, the reaction was in equilibrium. 1.51 kg/h of liquid product mixture containing 175 g/h methyl phenyl carbonate and 42 g/h diphenyl carbonate were continuously removed at the end of the third reactor and 1.27 kg/h of a mixture composed of methanol and dimethyl carbonate were removed at the head of the column mounted on the first reactor. That corresponds to a space-time yield for the methyl phenyl and diphenyl carbonate formation of 72 $g\times l^{-1}h^{-1}$. The selectivity in relation to the formation of aromatic carbonates was >99%.

Example 3

Example 2 was repeated in the apparatus described there and with the reaction conditions and starting product streams specified there. In addition, the liquid phase removed at the third reactor was fed continuously into a further stirred container (E in FIG. 2) having an internal volume of 2 l and a column mounted on it and it was continuously removed there again via a heated siphon with adjustable height. Said stirred container was heated to an internal temperature of 175° C. After 7 h, the reaction was in equilibrium. 1.47 kg/h of liquid phase containing 17.5 g/h methyl phenyl carbonate and 157 g/h diphenyl carbonate were continuously removed at the fourth stirred container. That corresponds to a space-time yield of the diphenyl carbonate and methyl phenyl carbonate formation of 35 $g\times l^{-1}h^{-1}$. The selectivity of the formation of the aromatic carbonates was >99%.

Comparison example

A heated stirred container having an internal volume of 2 l which was fitted with a 1.2 m long column filled with 6 mm glass rings was filled with 942 g of phenol and 21 g of titanium tetraphenolate. The contents of the container were preheated to 175° C. and dimethyl carbonate was added dropwise in such a way that the internal temperature was kept between 160° and 165° C. 155 g of dimethyl carbonate were added dropwise in the course of 4 h and, at the same time, a mixture composed of 17.4 g of methanol and 15.5 g of dimethyl carbonate was removed at the head of the column. After this time, the bottom product had the composition 854 g of phenol, 117 g of methyl phenyl carbonate, 26 g of diphenyl carbonate, 89 g of dimethyl carbonate and 3 g of byproducts. This gave a space-time yield for forming the aromatic carbonates of approximately 18 g.l$^{-1}$h$^{-1}$. The selectivity of the aryl carbonate formation was approximately 89%.

What is claimed is:

1. A process for producing an aromatic carbonate of the formula $$R^1-O-CO-O-R^2 \qquad (I)$$

in which

R$^2$ is phenyl or naphthyl and phenyl or naphthyl mono- to trisubstituted by straight-chain or branched C$_1$–C$_4$-alkyl, straight-chain or branched C$_1$–C$_4$-alkoxy, cyano and/or halogen, and R$^1$ assumes, independently of R$^2$, the scope of meaning of R$^2$ or straight-chain or branched C$_1$–C$_6$-alkyl, by catalyzed reaction of, in each case, 0.1–10 mol of an organic carbonate containing at least one aliphatic ester group of the formula $$R^1-OCOO-R^3 \qquad (II)$$

in which

R$^3$ is straight-chain or branched C$_1$–C$_6$-alkyl and

R$^1$ has the above scope of meaning, with 1 mol of a phenolic compound of the formula $$R^2-OX \qquad (III)$$

in which

R$^2$ has the above scope of meaning and

X represents hydrogen or —CO—O—C$_1$–C$_6$-alkyl containing a straight-chain or branched alkyl group, in the presence of a transesterification catalyst at 80°–350° C. and 10 mbar to 20 bar, wherein the reaction is carried out in at least two stirred containers connected one behind the other in such a way that the phenolic compound of the formula (III) is metered in liquid form into the first stirred container and the organic carbonate of the formula (II) is passed in gaseous form through said liquid phenolic compound in either cross current or counter current flow in one or more of the stirred containers and the reaction product of the formula (I) is removed in liquid form at the last stirred container and the product of the formula $$R^3-OX \qquad (IV)$$

in which

R$^3$ and X have the specified meaning is removed at the head of one or more stirred containers.

2. The process of claim 1, wherein 0.2–5 mol of the organic carbonate of the formula (II) is reacted with 1 mol of the phenolic compound of the formula (III).

3. The process of claim 2, wherein 0.5–3 mol of the organic carbonate of the formula (II) is reacted with 1 mol of the phenolic compound of the formula (III).

4. The process of claim 1, wherein the product of the formula (IV) is removed at the head of the first stirred container.

5. The process of claim 1, wherein the reaction is carried out in at least two stirred containers connected one behind the other in such a way that the organic carbonate of the formula (II) is metered into the last stirred container and the aromatic carbonate of the formula (I) is removed in liquid form at the last stirred container and the product of the formula (IV) is removed at the head of the first stirred container.

6. The process of claim 1, wherein the reaction is carried out in 2 to 10 stirred containers connected one behind the other.

7. The process of claim 6, wherein the reaction is carried out in 3 to 10 stirred containers connected one behind the other.

8. The process of claim 7, wherein the reaction is carried out in 3 to 8 stirred containers connected one behind the other.

9. The process of claim 1, which is carried out at 100°–250° C.

10. The process of claim 9, which is carried out at 120° to 240° C.

11. The process of claim 1, which is carried out in the pressure range from 0.05 to 15 bar.

12. The process of claim 11, which is carried out in the pressure range from 0.08 to 10 bar.

13. The process of claim 1, wherein a phenolic compound of the formula $$R^{12}-OH \qquad (V)$$

is used in which

R$^{12}$ is phenyl or phenyl monosubstituted by C$_1$–C$_4$-alkyl, C$_1$–C$_4$-alkoxy or chlorine.

14. The process of claim 13, wherein unsubstituted phenol is used.

15. The process of claim 1, wherein a symmetrical dialkyl carbonate of the formula $$R^3-O-CO-O-R^3 \qquad (VI)$$

in which

R$^3$ is straight-chain or branched C$_1$–C$_6$-alkyl, is used as organic carbonate containing at least one aliphatic ester group.

16. The process of claim 15, wherein dimethyl carbonate is used.

17. The process of claim 1, wherein the organic carbonate (II) is used as a mixture with 0–5% by weight, based on the weight of (II), of basic alcohol R$^3$—OH.

18. The process of claim 17, wherein the organic carbonate (II) is used as a mixture with 0.1–3% by weight, based on the weight of (II), of basic alcohol R$^3$—OH.

19. The process of claim 18, wherein the organic carbonate (II) is used as a mixture with 0.15–2% by weight, based on the weight of (II) of basic alcohol R$^3$—OH.

20. The process of claim 1, wherein the liquid reaction product of the last stirred container traverses a dwell-time section following said last stirred container.

* * * * *